United States Patent
Vega Romero

(10) Patent No.: US 11,721,022 B2
(45) Date of Patent: Aug. 8, 2023

(54) APPARATUS AND METHOD FOR AUTOMATED ANALYSES OF ULTRASOUND IMAGES

(71) Applicant: Exo Imaging, Inc., Santa Clara, CA (US)

(72) Inventor: Roberto Ivan Vega Romero, Edmonton (CA)

(73) Assignee: Exo Imaging, Inc., Santa Clara, CA (US)

( * ) Notice: Subject to any disclaimer, the term of this patent is extended or adjusted under 35 U.S.C. 154(b) by 288 days.

(21) Appl. No.: 17/135,408

(22) Filed: Dec. 28, 2020

(65) Prior Publication Data
US 2021/0201488 A1 Jul. 1, 2021

Related U.S. Application Data

(60) Provisional application No. 62/955,037, filed on Dec. 30, 2019.

(51) Int. Cl.
*G06K 9/00* (2022.01)
*G06T 7/00* (2017.01)
(Continued)

(52) U.S. Cl.
CPC ............ *G06T 7/0014* (2013.01); *G06N 3/08* (2013.01); *G16H 30/40* (2018.01); *G16H 50/20* (2018.01);
(Continued)

(58) Field of Classification Search
CPC ......... G06T 7/0014; G06T 2207/10132; G06T 2207/20084; G06T 2207/30004;
(Continued)

(56) References Cited

U.S. PATENT DOCUMENTS 8,891,881 B2  11/2014 Gupta et al.
2005/0020903 A1*  1/2005 Krishnan ............... G16H 50/20
                                                            600/407

(Continued)

FOREIGN PATENT DOCUMENTS

CN  107680678 A    2/2018
CN  109362221 A  *  2/2019  ............... A61B 8/46
(Continued)

OTHER PUBLICATIONS

International Search Report and Written Opinion dated Mar. 30, 2021 for PCT Application No. PCT/SG2020/050754, 9 pages.

*Primary Examiner* — Xin Jia
(74) *Attorney, Agent, or Firm* — Morgan, Lewis & Bockius LLP

(57) ABSTRACT

A non-transitory computer readable storage medium has instructions executed by a processor to execute a feature extractor to form extracted features from images formed by a first ultrasound scanner and a second ultrasound scanner. A decision maker is operated to form predictions of medical conditions based upon patterns identified in the extracted features. An evaluator is utilized to compare the predictions to labels in images to form a feature extractor performance measure and a decision maker performance measure. A dissimilarity estimator is operated to compute a difference measure between a probability distribution of features extracted from images formed by the first ultrasound scanner and the second ultrasound scanner.

19 Claims, 10 Drawing Sheets

(51) Int. Cl.
    *G16H 50/20*     (2018.01)
    *G06N 3/08*      (2023.01)
    *G16H 30/40*     (2018.01)

(52) U.S. Cl.
    CPC ............... *G06T 2207/10132* (2013.01); *G06T 2207/20084* (2013.01)

(58) Field of Classification Search
    CPC ...... G06T 7/0012; G06N 3/08; G06N 3/0472; G06N 3/088; G06N 3/0454; G06N 20/00; G16H 30/40; G16H 50/20
    See application file for complete search history.

(56) References Cited

U.S. PATENT DOCUMENTS

| | | |
|---|---|---|
| 2011/0082371 A1 | 4/2011 | Chono |
| 2012/0078099 A1 | 3/2012 | Suri |
| 2019/0041505 A1 | 2/2019 | Moradi et al. |

FOREIGN PATENT DOCUMENTS

| | | | |
|---|---|---|---|
| KR | 101977067 B1 | 5/2019 | |
| WO | WO-2020041881 A1 * | 3/2020 | ............... A61B 8/08 |

\* cited by examiner

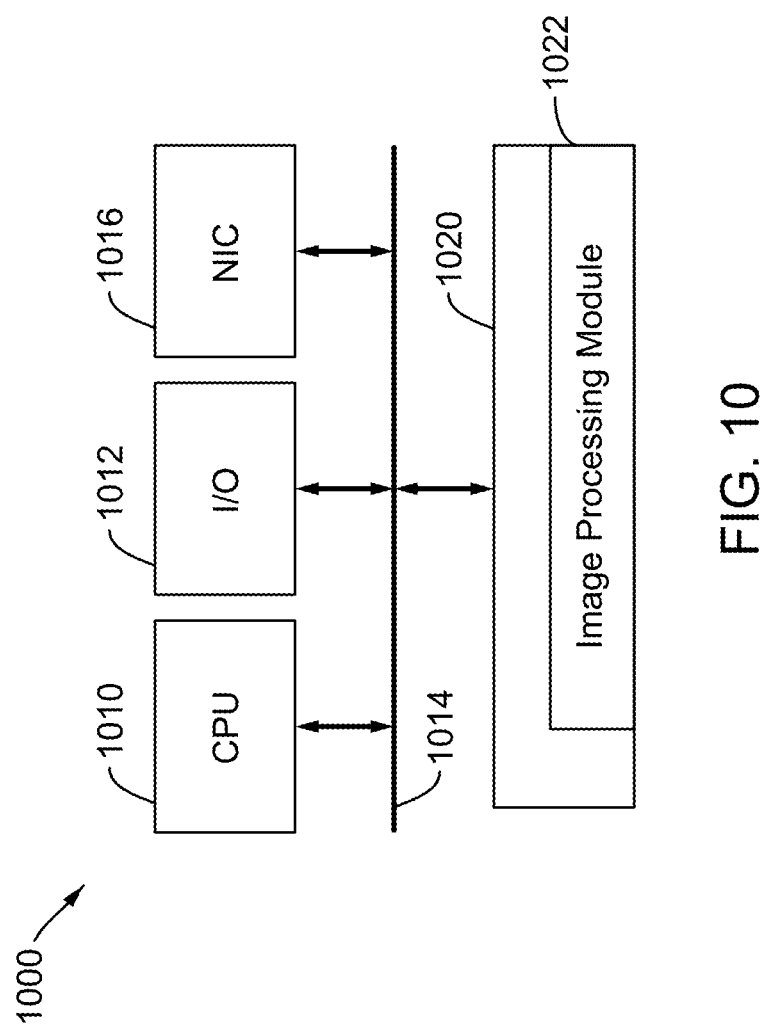

APPARATUS AND METHOD FOR AUTOMATED ANALYSES OF ULTRASOUND IMAGES

CROSS-REFERENCE TO RELATED APPLICATION

This application claims priority to U.S. Provisional Patent Application Ser. No. 62/955,037, filed Dec. 30, 2019, the contents of which are incorporated herein by reference.

FIELD OF THE INVENTION

This invention relates generally to image processing. More particularly, this invention is directed toward automated analyses of ultrasound images.

BACKGROUND OF THE INVENTION

Medical ultrasound is a non-invasive imaging modality that presents several advantages with respect to other imaging techniques: 1) it is non-ionizing—and is considered safe for human beings, 2) its cost is much lower than other imaging technologies, such as Magnetic Resonance Imaging (MRI) and Computed Tomography (CT) 3) it can be used in real time, and 4) it is portable and can be easily transported to the bedside of a patient. These characteristics make it one of the most commonly used imaging techniques for diagnosis.

Despite its popularity, one of the main drawbacks of this technique is that the interpretation of the results is very subjective. The accuracy of a diagnosis made, based on an ultrasound image, strongly depends on the experience of the medical expert who analyzes it. Additionally, research groups have analyzed reliability associated with ultrasound-based diagnosis and they found it is far from optimal.

Besides the subjective nature of the imaging-based diagnosis, an important problem is the fatigue experienced by busy radiologists who analyze these images. It is well documented that fatigue is an important source of medical errors, and it might be exacerbated by excessive workload, cognitive overload, imperfect information processing and flawed decision making.

These two problems prompted the development of Computer Assisted Diagnosis (CAD) systems, which aim to quantify relevant features from the image and reduce the workload on radiologist by helping them in the diagnosis process. State-of-the-art systems receive an ultrasound image as an input, and use machine learning, computer vision, and statistical techniques to analyze it and provide a diagnosis. Unfortunately, research shows that these automated approaches tend to be customized to a particular ultrasound-scanner. In other words, an algorithm that works well in images acquired by one scanner is not guaranteed to work well in images acquired with a different scanner. An algorithm may also be less effective even on images from the same scanner when performed with different transducers and different settings for parameters such as focus, intensity/brightness and Doppler scale.

In general, Computer Aided Diagnosis systems require a training phase. During this training phase the system 'learns', from labeled data, the appropriate patterns that allows it to deliver a correct diagnosis. Once trained, the system can be applied to new images whose diagnosis is unknown. These machine learning algorithms assume that the probability distribution of the training data and the new data is similar; however, they might fail when this assumption is not met. Images obtained with different ultrasound machines are different depending on the characteristics of the scanner, such as frequency of the ultrasound wave, ability of the technician acquiring the image, parameters used to obtain the image. This causes the final distribution of the values of the pixels to change from one machine to another, reducing the performance of machine learning approaches. An example of this case can be seen in FIG. 6. This figure corresponds to ultrasound images of the hip taken with different scanners, or different settings of the scanner. It is possible to appreciate differences in the resolution, brightness, noise, and sharpness of the image. These differences might cause machine learning algorithms to fail.

Most of the current machine learning methods approach this problem by 1) creating a vast training set comprising images acquired from different scanners, or 2) building a different CAD system for each ultrasound machine. Unfortunately, these solutions require a labeled dataset from every scanner, which is highly time consuming, tedious, and rarely available.

Thus, there is a need to address the foregoing problems associated with ultrasound image analyses.

SUMMARY OF THE INVENTION

A non-transitory computer readable storage medium has instructions executed by a processor to execute a feature extractor to form extracted features from images formed by a first ultrasound scanner and a second ultrasound scanner. A decision maker is operated to form predictions of medical conditions based upon patterns identified in the extracted features. An evaluator is utilized to compare the predictions to labels in images to form a feature extractor performance measure and a decision maker performance measure. A dissimilarity estimator is operated to compute a difference measure between a probability distribution of features extracted from images formed by the first ultrasound scanner and the second ultrasound scanner.

BRIEF DESCRIPTION OF THE FIGURES

The invention is more fully appreciated in connection with the following detailed description taken in conjunction with the accompanying drawings, in which:

FIG. 10 illustrates a computer configured in accordance with an embodiment of the invention.

Like reference numerals refer to corresponding parts throughout the several views of the drawings.

DETAILED DESCRIPTION OF THE INVENTION

Figures 7A, 7B, 7C:
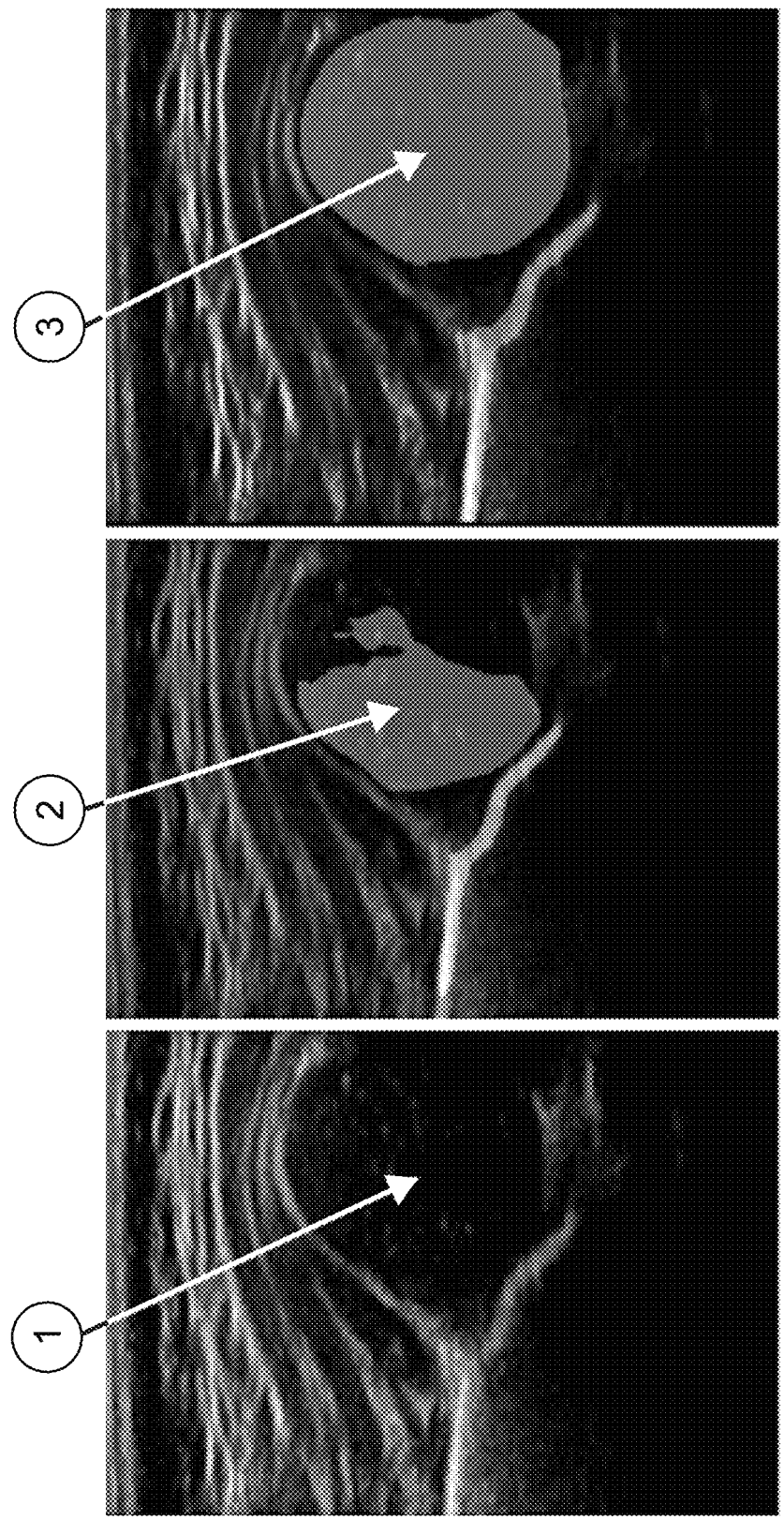
FIGS. 7A, 7B and 7C are examples of the output predicted by an automatic segmentation algorithm whose objective is to create masks of the acetabulum and femoral head in an ultrasound image of the hip.

We propose a method to automatically adapt a CAD system, trained to work with ultrasound images extracted from a first scanner (Scanner 1 or Data Machine 1), to work properly with ultrasound images extracted from a second scanner (Scanner 2 or Data Machine 2). This adaptation method works without the need for human intervention, other than providing the input information to be analyzed. The CAD system consists of three basic modules: a feature extractor, a decision maker, and an evaluator. A fourth module, called the dissimilarity estimator, is added to the main CAD system to allow the adaptation to images obtained from different machines. The advantages of this automatic adaptation is illustrated in FIGS. 7A, 7B and 7C. FIG. 7A depicts a typical image of the hip. The objective in this case is to segment two anatomical regions of interest: the acetabulum and the femoral head. When there is no correction for the differences in the scanner, the automatic segmentation process might be suboptimal, as shown in FIG. 7B. On the other side, after correcting for these differences using the method described herein the quality of the segmentation is greatly improved, as shown in FIG. 7C.

The CAD system requires as an input a series of ultrasound images from a scanner 1, along with associated labels of every image. The first step is a pre-processing stage aimed at standardizing the brightness and deformations of the images, as well as removing all components that are not part of the ultrasound image. The system then uses the feature extractor to identify characteristics in the image that differentiates between different labels. The extracted features go to the decision maker module, which analyzes the extracted features to provide a suggested diagnosis. Finally, the diagnosis suggested by the Computer Aided Diagnosis system, along with the diagnosis provided by a medical expert will go into the evaluator module to check the performance of the CAD system. This performance is used to provide feedback to the feature extractor and the decision maker to modify them in an effort to improve performance. This constitutes the basic CAD system that will work correctly with images acquired from Scanner 1.

There are three different ways in which the adaptation method might work, depending on the available data: 1) When labeled data from machine 1, and few instances of the dataset from machine 2 are available 2) When labeled data from machine 1, and completely unlabeled data from machine 2 are available. 3) When only a fully labeled dataset from machine 2 is available.

Figure 1:
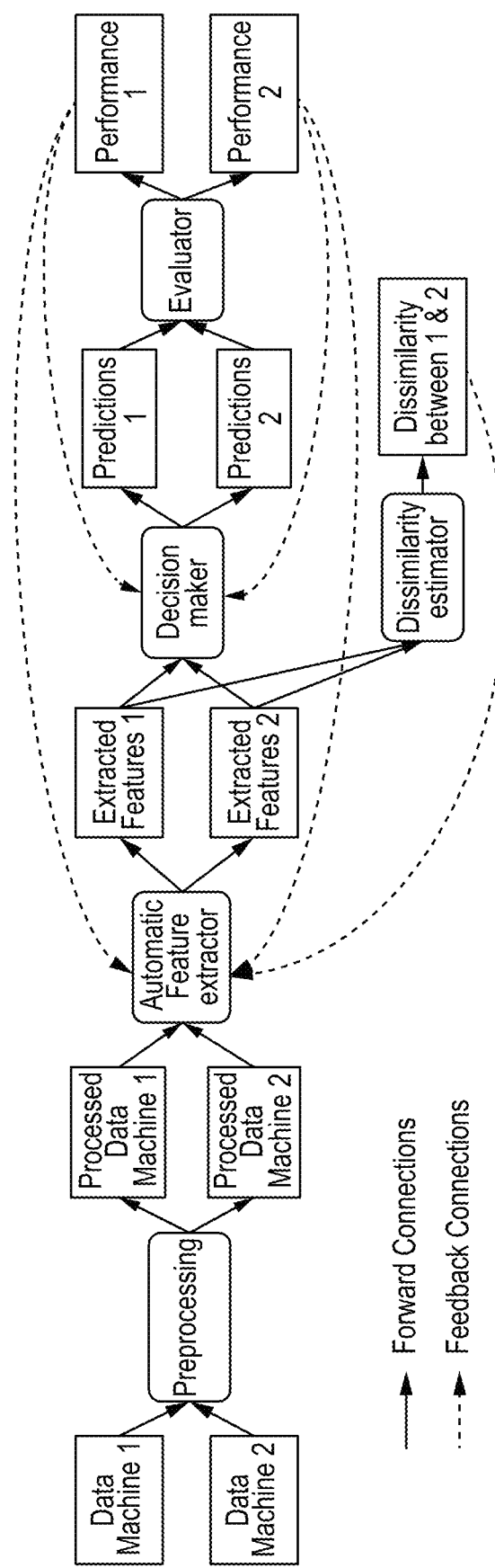
FIG. 1 illustrates training associated with two machines where performance and dissimilarities between extracted features modify parameters of the feature extractor and decision maker.
Figure 3:
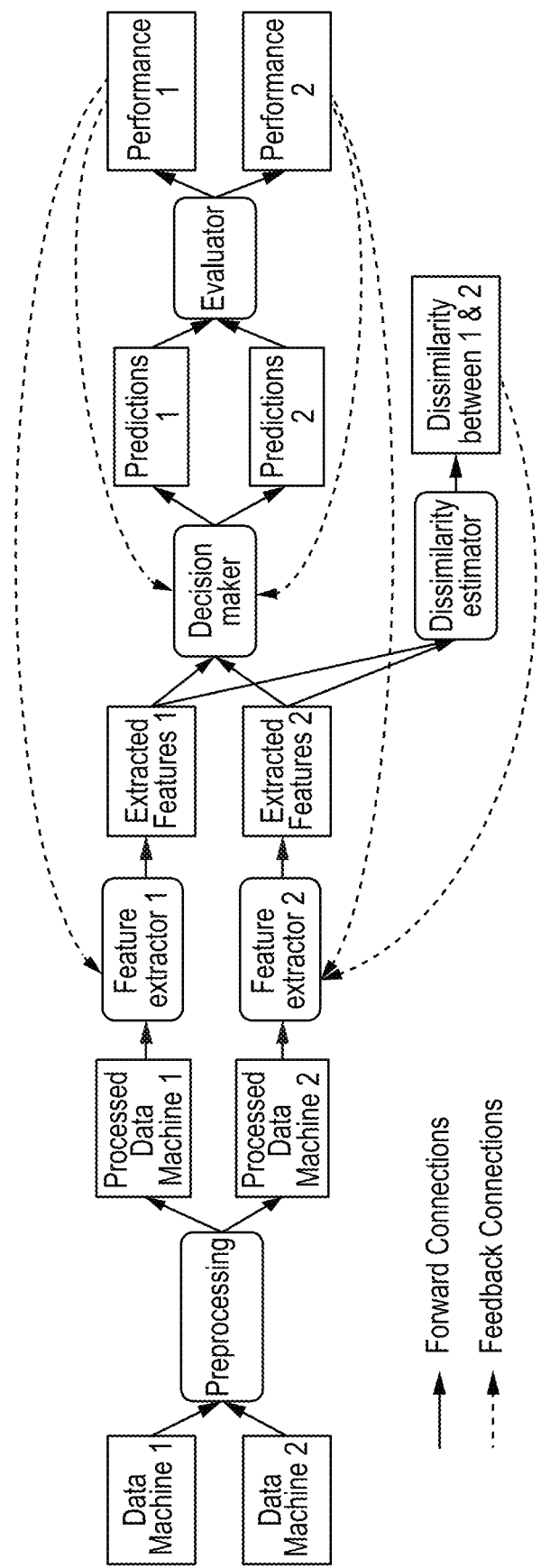
FIG. 3 illustrates processing similar to FIG. 1 but utilizing two separate feature extractors.

Case 1, illustrated in FIG. 1. To adapt the basic CAD system to work properly with images obtained from a machine 2, we add a dissimilarity estimator module. The feature extractor receives as an input a batch of pre-processed images from the machine 1, and a batch of pre-processed images from machine 2. It produces the extracted features from machine 1, and the extracted features from machine 2. These extracted features from both machines are the input to the dissimilarity estimator. The objective of the dissimilarity estimator is to provide feedback to the feature extraction module, such that the probability distribution of the extracted features from both machines are as close as possible. Additionally, since we have a few labeled instances from the second machine, we can pass these instances, along with the instances of machine 1, through the decision maker and evaluator, and then use their performance to provide feedback to the feature extractor and decision maker. Optionally, it is possible to have a different feature extraction process for data extracted from a different scanner. This sub-case is depicted in FIG. 3, which has separate feature extractors: Feature extractor 1 and Feature extractor 2.

Figure 4:
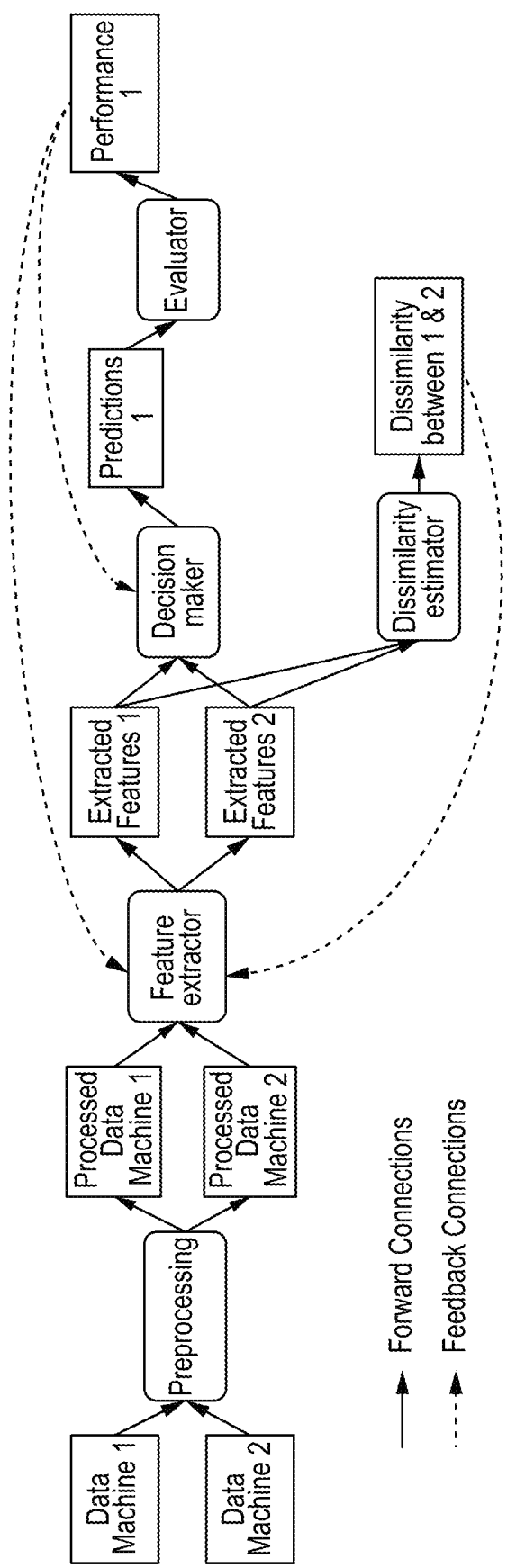
FIG. 4 illustrates training associated with unlabeled data where dissimilarity between extracted features is computed.

Case 2 is illustrated in FIG. 4. The dissimilarity module is used identically as in case 1; however, since labeled data is not available for machine 2 feedback is provided to the decision maker and feature extractor using the performance of the instances of machine 1.

Figure 5:
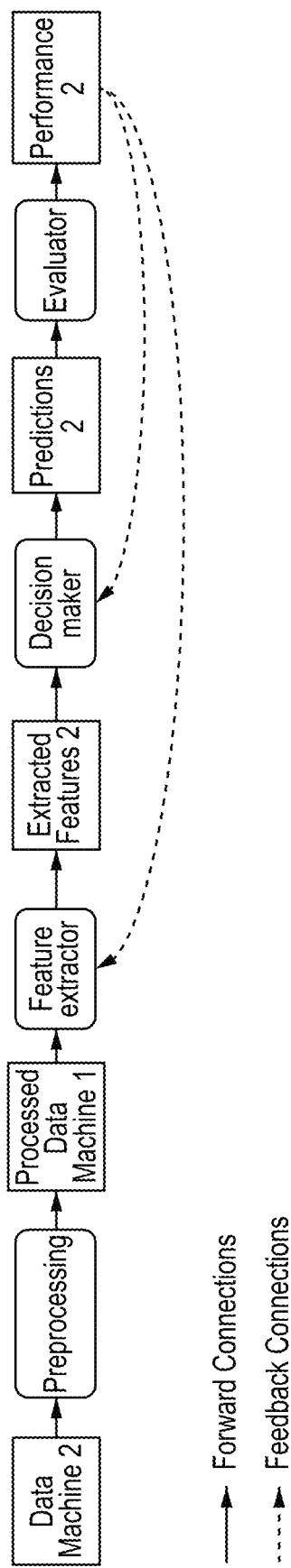
FIG. 5 illustrates a scenario where data from a first machine is used for training a feature extractor and decision maker which are then used by a second machine utilizing performance measures on a labeled set.

Case 3 is illustrated in FIG. 5. We no longer have access to the data from machine 1, but we can use the feature extractor and decision maker learned using the basic CAD system. We can then use the data from machine 2 to 'fine-tune' these 2 modules to work properly on this data.

The invention adapts a CAD system, trained to work on images acquired with an ultrasound machine 1, to work properly on images acquired with another ultrasound machine 2. By properly we mean that the diagnosis accuracy on both machines should be similar and should be clinically relevant.

Figure 6A:
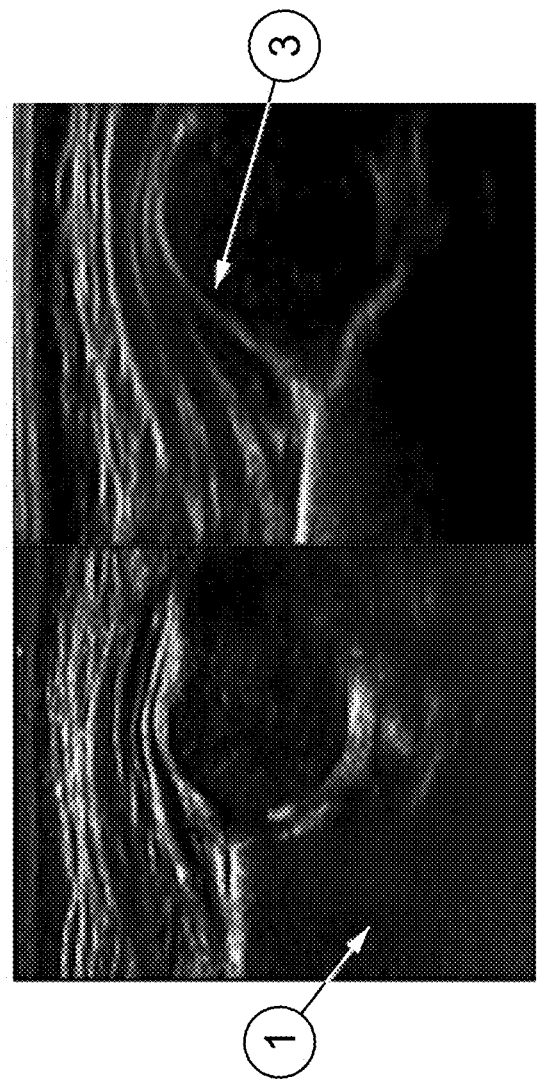
FIGS. 6A and 6B are examples of the different quality of images acquired with scanners of different vendors, and under different settings.
Figure 6B:
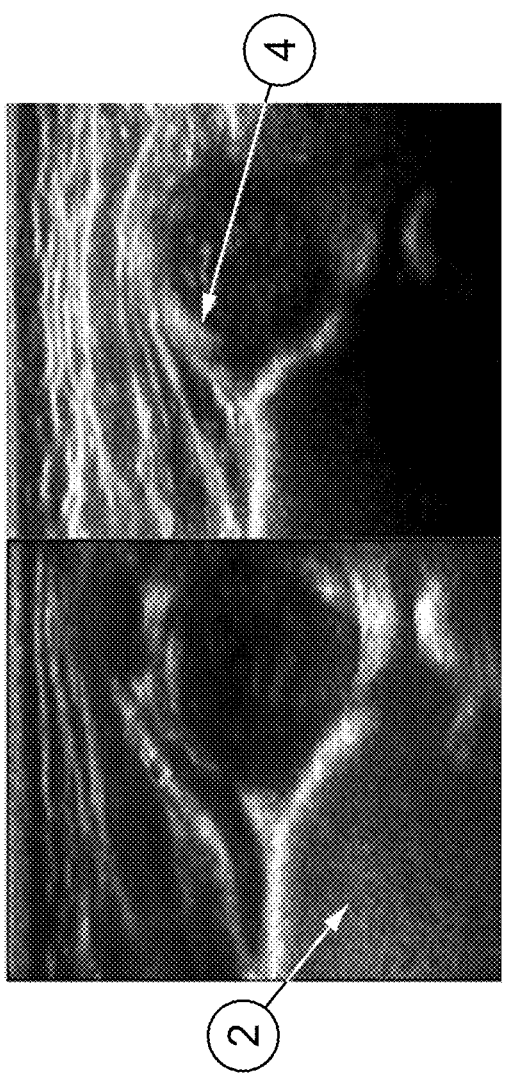

FIGS. 6A and 6B depict some of the differences in the quality of images acquired with different scanners. Note that it is possible to visually identify differences in the brightness, sharpness, noise level, and resolution among the images. FIG. 6A was acquired with one scanner, while FIG. 6B was acquired with a different machine. It is possible to appreciate differences in the levels of speckle noise, intensity, and sharpness of the images. The region indicated by markers 1 and 2 show a difference in texture in the area below the acetabular bone. While the region indicated by marker 1 is almost completely dark, the region indicated by marker 2 presents a higher intensity. Also, it is possible to distinguish a difference in the sharpness of the regions highlighted by markers 3 and 4. While the boundaries in the exterior layer of the femoral head are well defined in the image indicated by marker 3, a similar area highlighted by marker 4 is blurrier.

In computational terms, this means that the distribution of intensity values will be different for different scanners (or settings of the scanner), which might cause CAD systems to underperform. The presented method can adapt the CAD system, to correct for this problem under three different scenarios:

1. When labeled subset of the data from a machine 1 and a labeled subset of the data from a machine 2 are available.
2. When labeled data from a machine 1 and unlabeled data from a machine 2 are available.
3. When labeled data from a machine 2 and the learned feature extraction and decision making modules trained using data from a machine 1 are available.

FIG. 1 shows the adaptation method for the first scenario. The two initial blocks, Data Machine 1, and Data Machine 2 represent the available training set. We assume that at least a subset from the data acquired from every scanner is labeled. For example, we might collect n ultrasound images from the scanner 1, and m ultrasound images from scanner 2. We assume that at least x out of the n images from scanner 1 and at least y out of m images from the scanner 2 are labeled. The labels might be a diagnosis (for example normal vs. fatty liver), or a segmentation mask (a mask indicating which pixels correspond to the anatomical structure of interest, or to a lesion within the image).

The blocks Data Machine 1, and Data Machine 2 are the input to the Feature Extractor block. Intuitively, the Feature Extractor block has the objective of transforming the original, raw data, into a new mathematical representation. This mathematical representation ideally contains patterns that lead to a successful classification, segmentation, or regression.

Feature Extractor block can be, for example, a mathematical function applied over each of the images. This mathematical function contains trainable parameters that can be optimized to minimize a previously determined cost function. For the case of images, a common way of representing this mathematical operation is through a convolutional neural network (CNN), whose output are Extracted Features 1 and Extracted Features 2. The Feature Extractor block can be trained from scratch, or it can be a Feature Extractor block previously trained with data from Machine 1, another external dataset, or a combination of both.

Figure 8:
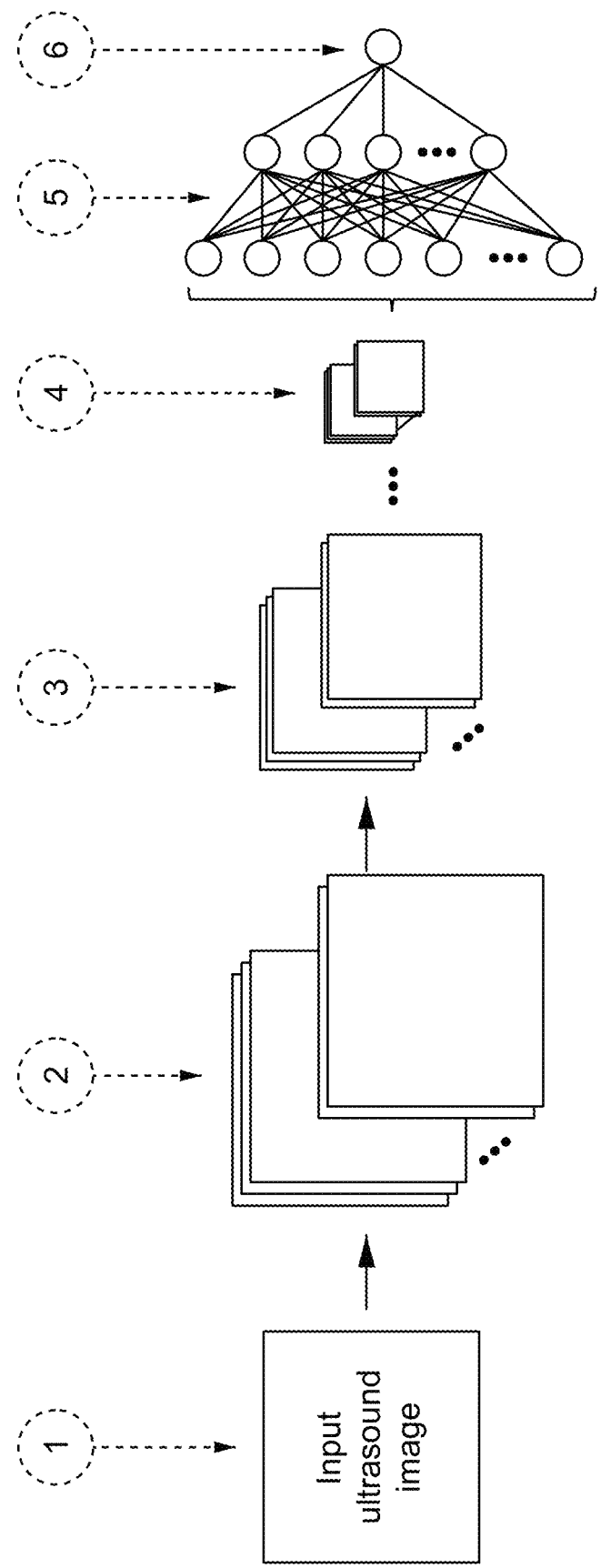
FIG. 8 Illustrates an automatic feature extractor configured as a series of convolutional layers and the decision maker is represented by fully connected layers.

FIG. 8 shows a possible implementation of the Feature Extractor block. This figure depicts a series of convolutional layers, followed by pooling layers, that will learn a representation of the data that can then be used for prediction purposes. Marker 1 points to a representation of an ultrasound image, which is the input to the system. Marker 2 indicates the first convolutional and pooling layers. Marker 3 points to the second convolutional and pooling layer. It is possible to continue stacking these layers to achieve the desired depth. Marker 4 points to the n-th convolutional and pooling layer.

Under ideal circumstances, the probability distribution of a batch of Extracted Features 1 should be similar to the probability distribution of a batch of Extracted Features 2. This is often not the case because of different noise pattern introduced by different scanners, as well as differences in hardware and postprocessing of the data done internally by every scanning device. A further source of differences is different patient populations scanned at Machine 1 and Machine 2.

Figure 9:
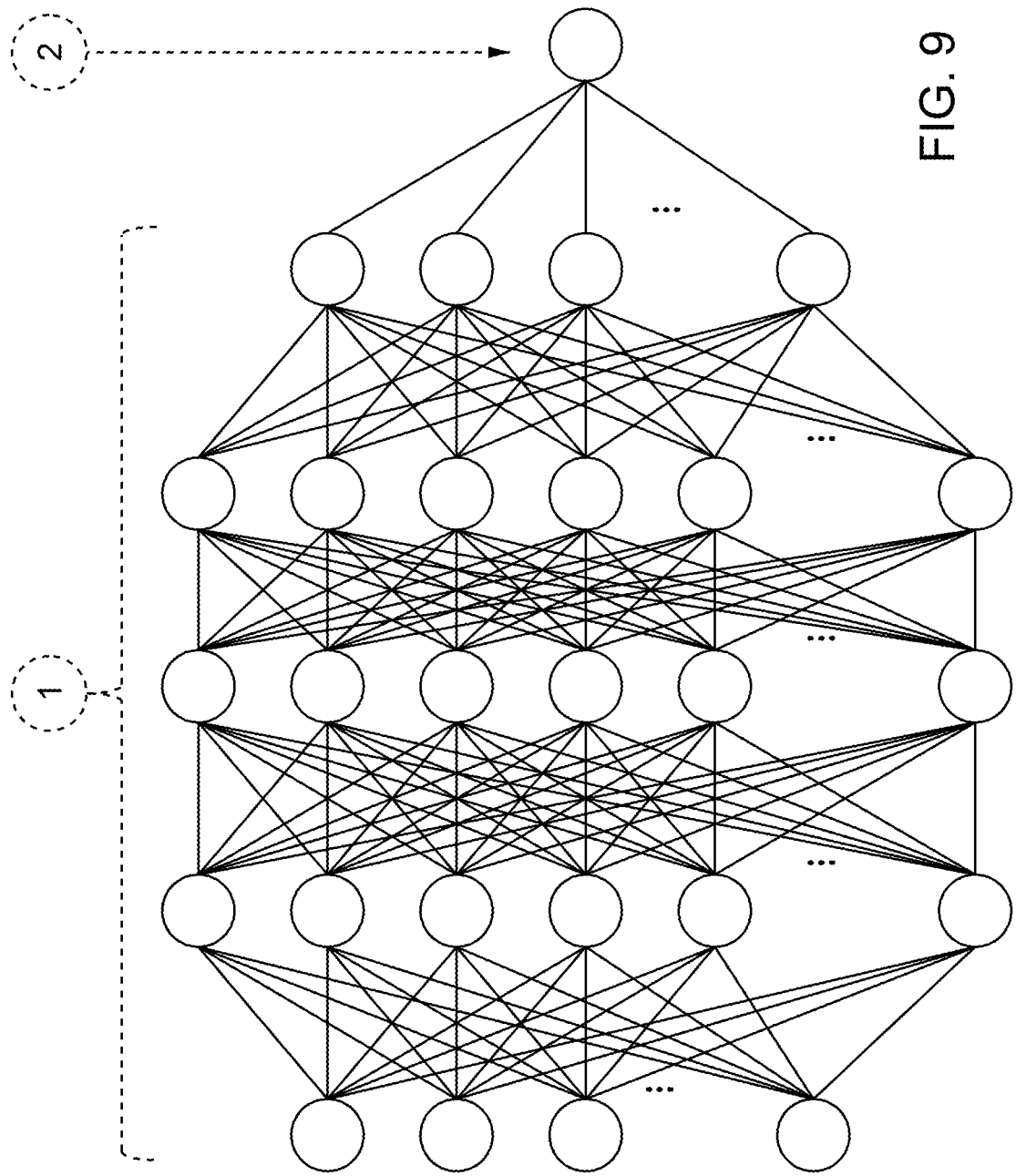
FIG. 9 illustrates the dissimilarity block as a neural network trained to estimate the Wasserstein distance between samples of different probability distributions up to a constant.

The block Dissimilarity Estimator computes a distance that quantifies the difference between the distribution of the features extracted by both scanning devices. An example of such a measurement can be as simple as correcting for the spacing in the pixel space, or as complex as computing the Kullback-Leibler divergence, or the Wasserstein distance. This latter distance can be efficiently approximated (under some mild assumptions) via a neural network configuration named Wasserstein-Generative Adversarial Network. FIG. 9 shows a possible implementation of a neural network that estimates the Wasserstein distance, up to a multiplicative constant factor. The marker 1 points to the 'hidden layers' of the neural network, which compute an approximation to the Wasserstein distance. Marker 2 points to the output node, whose value is the estimated distance between probability distributions. The objective of this block is to compute the dissimilarity between the features extracted from both machines, and then use this dissimilarity to update the trainable parameters of the Feature Extractor block. The rationale is that after the training process is complete, the Feature Extractor will be optimized to minimize the dissimilarity between the Extracted Features 1 and Extracted Features 2. Since the Feature Extractor is additionally being modified by the Performance 1 and Performance 2 blocks, the final parameters learned by the Feature Extractor block will be a trade-off between the performance and dissimilarity objectives. The user of the proposed adaptation method can decide which objective, and by how much, has priority.

FIG. 7A depicts an example of an input image. Marker 1 indicates the location of the femoral head. FIG. 7B shows the output predicted by an algorithm that does not correct for differences in the scanner. The marker 2 points to the area that the algorithm predicts contains the femoral head. Note how this algorithm misses almost half of the femoral head. FIG. 7C shows the output predicted by our method of automatically correcting for differences across scanners. Marker 3 indicates the area predicted to be the femoral head. Note how, after correcting for differences across scanners, the algorithm is able to capture the entire femoral head. FIG. 7B and FIG. 7C show the effect of correcting for differences in the scanners in the predicted output of a segmentation task. When no correction is applied, the segmentation algorithms underperforms, as shown in FIG. 7B, since it cannot capture the round shape of the femoral head. On the other hand, when we use the automatic correction method described in this patent, the quality of the segmentation algorithm greatly increases. For this example, the distance computed is the difference in spacing and histogram intensities among the images.

Additionally, the Extracted Features 1 and Extracted Features 2 corresponding to the labeled instances of the Data Machine 1, and Data Machine 2 are used as an input to the block Decision Maker. The Extracted Features 1 and Extracted Features 2 corresponding to the unlabeled instances are not required in this step. The objective of this block is to find patterns in the extracted features that minimize the error between the predictions of the CAD system and the labels provided along with the training dataset.

The Decision Maker block is also a mathematical function with learnable parameters that maps the Extracted Features 1 and Extracted Features 2 to the Predictions 1 and Predictions 2. Depending on the complexity of the model, this mathematical function can be as simple as a thresholding operation, or it can be a function learned by any of the available machine learning algorithms, such as logistic regression, linear regression, support vector machines, neural networks, probabilistic models, etc. The output of this block, Predictions 1 and Predictions 2, are computational objects that have the same shape as the original labels of the training data. The fully connected layers in FIG. 8 illustrate a possible implementation of the Decision Maker block. Marker 5 points to a fully connected layer, which fulfills the role of the decision maker. Finally, Marker 6 points to the output node of the network, which outputs the medical prediction made by the system. This prediction is usually a category, such as normal, mild-fatty, moderately fatty or severely fatty for the problem of identifying the degree of fatness in the liver.

The computational objects Predictions 1 and Predictions 2 become then the input to the block Evaluator. This block compares the predictions with the labels provided as part of the training set and computes a number that reflects how accurate the predictions are. Once again, the evaluator is a mathematical function whose specific form depends on the task objective. For example, in classification tasks the cross-entropy is a common cost function, while in regression tasks the mean squared error is commonly used. The cost function in this block can be tailored to guide the CAD system to have some properties, such as low complexity, sparsity, group sparsity, etc. The output of the Evaluator block will be Performance 1 for Predictions 1, and Performance 2 for Predictions 2. The performance measure will be finally used to update the learnable parameters of the blocks Feature Extractor and Decision maker.

The process described in this section is performed iteratively until a stop condition is reached. This stop condition might be, for example, a predetermined number of iterations, when changes in the performance metric is lower than a predefined threshold, etc.

Figure 2:
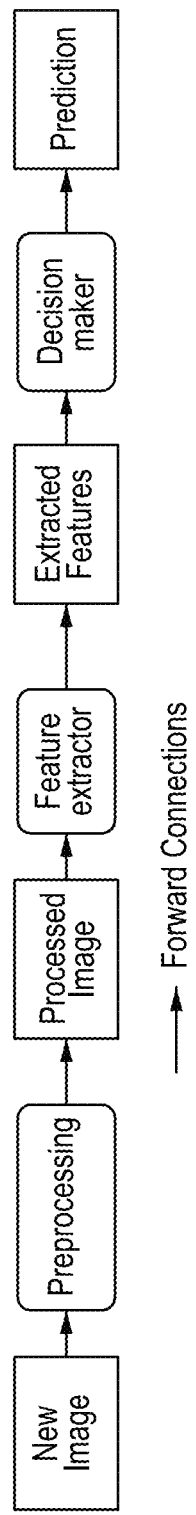
FIG. 2 illustrates general workflow after training.

Once the adaptation process has finished, i.e., the stop condition has been reached, it is possible to use the learned blocks Feature extractor and Decision maker to make predictions on new, previously unseen images. This process is illustrated in FIG. 2. The new images might be generated by either the scanning machine 1 or the scanning machine 2.

FIG. 3 depicts a variation of the process described in FIG. 1. In this variation there are two different feature extraction blocks: Feature extraction 1 and Feature extraction 2. These blocks receive Data Machine 1 and Data Machine 2, respectively, as inputs to produce the computational objects Extracted Features 1 and Extracted Features 2. The difference with respect to the method in FIG. 1 is that having different feature extraction methods allow for further flexibility when trying to match the distribution of the features extracted. A second difference is that the block Features extracted 1 is updated by the computational object Performance 1, but not by the computational objects Performance 2 nor Dissimilarity between 1 & 2. The block Features extracted 2, on the other side, is updated by the computational objects Performance 2 and Dissimilarity between 1 & 2; but not by the computational object Performance.

FIG. 4 depicts a variation of the process described in FIG. 1. Now the assumption is that none of the images from the machine 2 are labeled. For example, we might collect n ultrasound images from the scanner 1, and m ultrasound images from scanner 2. Then at least x out of the n images from scanner 1 are labeled, but none of the m ultrasound images from scanner 2 are.

The blocks Feature extractor and Dissimilarity estimator work exactly the same as before. The block Decision maker, on the other side, receives now only the computational object Features extracted 1. The Decision maker outputs the computational object Predictions 1. Predictions 1 goes into the block Evaluator, which outputs the computational object Performance 1. The method then uses Performance 1 to update the learnable parameters of the blocks Feature Extractor and Decision maker. The main difference between the methods depicted in FIG. 1 and FIG. 4 is that the learnable parameters of the block Feature Extractor are updated using information from the computational objects Dissimilarity between 1 & 2, Performance 1 and Performance 2 in the method described in FIG. 1. For the method in FIG. 4, the block Feature Extractor is updated using information from the computational objects Dissimilarity between 1 & 2 and Performance 1, but not the computational object Performance 2. Similarly, in the method described in FIG. 1, the block Decision maker is updated using information from the computational objects Performance 1 and Performance 2. The method depicted in FIG. 4, on the other side, updates the learnable parameters of the block Decision maker using the computational object Performance 1, but not Performance 2.

FIG. 5 depicts another variation of the method presented in FIG. 1. For this method, the assumption is that the blocks Feature extractor and Decision maker were previously trained with an external dataset that is no longer available. Additionally, we assume that the block Data Machine 2 contains data that is fully labeled. For example, we might collect m ultrasound images from scanner 2, and all m images are labeled.

The method shown in FIG. 5 starts by using the previously learned blocks Feature extractor and Decision maker as well as the block Evaluator to compute the computational objects Features extracted 2, Predictions 2, and Performance 2. It will then use the computational object Performance 2 to update the learnable parameters of the blocks Feature extractor and Decision maker. This process is performed iteratively until a stop condition is reached. This stop condition might be, for example, a predetermined number of iterations, when changes in the performance metric is lower than a predefined threshold, etc.

FIG. 10 illustrates a machine 1000 configured to implement the disclosed processing operations. A processor 1010 is connected to input/output devices 1012 via a bus 1014. A network interface circuit 1016 is also connected to the bus 1014 to provide connectivity to a network (not shown). A memory 1020 is also connected to the bus 1014. The memory 1020 stores an image processing module 1022 with instructions executed by processor 1010 to implement the processing operations disclosed herein. That is the image processing module 1022 implements such disclosed operations as preprocessing, automatic feature extraction, the decision maker, the evaluator, the dissimilarity estimator and the like.

An embodiment of the present invention relates to a computer storage product with a computer readable storage medium having computer code thereon for performing various computer-implemented operations. The media and computer code may be those specially designed and constructed for the purposes of the present invention, or they may be of the kind well known and available to those having skill in the computer software arts. Examples of computer-readable media include, but are not limited to: magnetic media such as hard disks, floppy disks, and magnetic tape; optical media such as CD-ROMs, DVDs and holographic devices; magneto-optical media; and hardware devices that are specially configured to store and execute program code, such as application-specific integrated circuits ("ASICs"), programmable logic devices ("PLDs") and ROM and RAM devices. Examples of computer code include machine code, such as produced by a compiler, and files containing higher-level code that are executed by a computer using an interpreter. For example, an embodiment of the invention may be implemented using JAVA®, C++, or other object-oriented programming language and development tools. Another embodiment of the invention may be implemented in hard-wired circuitry in place of, or in combination with, machine-executable software instructions.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

The invention claimed is:

1. A non-transitory computer readable storage medium with instructions for execution by a processor, including instructions for:
training a machine learning model to analyze ultrasound data acquired using different ultrasound scanners by:
executing a feature extractor to form extracted features from images formed by a first ultrasound scanner and a second ultrasound scanner;
operating a decision maker to form predictions of medical conditions based upon patterns identified in the extracted features;
utilizing an evaluator to compare the predictions of medical conditions to labels in at least a subset of the images to form a feature extractor performance measure;
operating a dissimilarity estimator to compute a difference measure between the extracted features formed by the first ultrasound scanner and the extracted features formed by the second ultrasound scanner; and
updating one or more parameters of the feature extractor based on the feature extractor performance measure and the computed difference measure, so as to minimize a dissimilarity between the extracted features from the first ultrasound scanner and the second ultrasound scanner.

2. The non-transitory computer readable storage medium of claim 1 wherein the instructions for executing the feature extractor include instructions for:
executing a first feature extractor to extract features from images formed by the first ultrasound scanner; and
executing a second feature extractor to extract features from images formed by the second ultrasound scanner.

3. The non-transitory computer readable storage medium of claim 1, wherein the labels are solely associated with images formed by the first ultrasound scanner.

4. The non-transitory computer readable storage medium of claim 1, wherein the feature extractor comprises a plurality of convolution neural network processing layers.

5. The non-transitory computer readable storage medium of claim 1, wherein the decision maker is a fully connected neural network.

6. The non-transitory computer readable storage medium of claim 1, wherein the dissimilarity estimator is a fully connected neural network.

7. The non-transitory computer readable storage medium of claim 1, further including instructions for:
utilizing the evaluator to compare the predictions of medical conditions to the labels in at least a subset of the images to form a decision maker performance measure, wherein the decision maker performance measure is used to refine one or more parameters of the decision maker.

8. A non-transitory computer readable storage medium with instructions for execution by a processor, including instructions for:
updating a trained model for analyzing ultrasound data acquired using different ultrasound scanners by:
executing a feature extractor that has been trained on images from a first ultrasound scanner, to extract features from images formed by a second ultrasound scanner, distinct from the first ultrasound scanner;
operating a decision maker that has been trained on the images from the first ultrasound scanner to form predictions of medical conditions based upon patterns identified in the extracted features;
utilizing an evaluator to compare the predictions of medical conditions to labels corresponding to the images from the second ultrasound scanner to form a feature extractor performance measure and a decision maker performance measure; and
updating one or more parameters of the feature extractor and the decision maker based on the feature extractor performance measure and the decision maker performance measure.

9. The non-transitory computer readable storage medium of claim 8, wherein the feature extractor comprises a plurality of convolution neural network processing layers.

10. The non-transitory computer readable storage medium of claim 8, wherein the decision maker is a fully connected neural network.

11. The non-transitory computer readable storage medium of claim 8, wherein the feature extractor performance measure is used to refine the one or more parameters of the feature extractor.

12. The non-transitory computer readable storage medium of claim 8, wherein the decision maker performance measure is used to refine the one or more parameters of the decision maker.

13. A computer system, comprising:
one or more processors; and
memory storing one or more programs, the one or more programs including instructions for:
training a machine learning model to analyze ultrasound data acquired using different ultrasound scanners by:
executing a feature extractor to form extracted features from images formed by a first ultrasound scanner and a second ultrasound scanner;
operating a decision maker to form predictions of medical conditions based upon patterns identified in the extracted features;
utilizing an evaluator to compare the predictions of medical conditions to labels in at least a subset of the images to form a feature extractor performance measure;
operating a dissimilarity estimator to compute a difference measure between the extracted features formed by the first ultrasound scanner and the extracted features formed by the second ultrasound scanner; and
updating one or more parameters of the feature extractor based on the feature extractor performance measure and the computed difference measure, so as to minimize a dissimilarity between the extracted features from the first ultrasound scanner and the second ultrasound scanner.

14. The computer system of claim 13 wherein the instructions for executing the feature extractor include instructions for:
executing a first feature extractor to extract features from images formed by the first ultrasound scanner; and
executing a second feature extractor to extract features from images formed by the second ultrasound scanner.

15. The computer system of claim 13, wherein the labels are solely associated with images formed by the first ultrasound scanner.

16. The computer system of claim 13, wherein the feature extractor comprises a plurality of convolution neural network processing layers.

17. The computer system of claim 13, wherein the decision maker is a fully connected neural network.

18. The computer system of claim 13, wherein the dissimilarity estimator is a fully connected neural network.

19. The computer system of claim 13, wherein the memory further stores instructions for:
- utilizing the evaluator to compare the predictions of medical conditions to the labels in at least a subset of the images to form a decision maker performance measure, wherein the decision maker performance measure is used to refine one or more parameters of the decision maker.

* * * * *